US010539547B2

(12) United States Patent
Pigeon et al.

(10) Patent No.: US 10,539,547 B2
(45) Date of Patent: Jan. 21, 2020

(54) FUEL COMPATIBILITY AND STABILITY ANALYZER

(71) Applicant: AD Systems S.A.S., Saint André sur Orne (FR)

(72) Inventors: Didier Pigeon, Ifs (FR); Martial Lépinay, Mouen (FR)

(73) Assignee: AD Systems S.A.S., Saint-André-sur-Orne (FR)

( * ) Notice: Subject to any disclaimer, the term of this patent is extended or adjusted under 35 U.S.C. 154(b) by 80 days.

(21) Appl. No.: 15/830,247

(22) Filed: Dec. 4, 2017

(65) Prior Publication Data

US 2018/0156771 A1 Jun. 7, 2018

Related U.S. Application Data

(60) Provisional application No. 62/429,624, filed on Dec. 2, 2016.

(51) Int. Cl.
*G01N 33/28* (2006.01)
*G06T 7/90* (2017.01)
(Continued)

(52) U.S. Cl.
CPC ......... *G01N 33/28* (2013.01); *G01N 21/5911* (2013.01); *G06T 7/001* (2013.01);
(Continued)

(58) Field of Classification Search
CPC ............... G01N 21/5911; G01N 33/28; G01N 2021/5915; G01N 2021/5957;
(Continued)

(56) References Cited

U.S. PATENT DOCUMENTS

| 4,781,892 A | * | 11/1988 | Dickakian | ............. | G01N 30/90 210/198.3 |
| 5,313,824 A | * | 5/1994 | Herguth | ............ | G01N 33/2888 356/421 |

(Continued)

FOREIGN PATENT DOCUMENTS

| FR | 2965924 B1 | * | 12/2012 | ......... G01N 33/2888 |
| JP | H02-248861 A | | 10/1990 | |

OTHER PUBLICATIONS

International Search Report for PCT/IB2017/001798 published Nov. 8, 2018. (Year: 2018).*

(Continued)

*Primary Examiner* — Brenda C Bernardi
(74) *Attorney, Agent, or Firm* — Vorys, Sater, Seymour and Pease LLP; Vincent M DeLuca

(57) ABSTRACT

Fuel sampling systems are disclosed. In one embodiment, a fuel sampling system includes an optical capture device and an analysis computing device that stores logic for implementing an evaluation sequence. During the evaluation sequence, the analysis computing device performs at least the following: receive a captured image from the optical capture device, identify areas of highest contrast in the captured image, and determine if the areas of highest contrast define a ring. If the areas of highest contrast define a ring, evaluate a contrast ratio between the ring and areas outside of the ring, and determine if the captured image reflects a fuel sample that exceeds a predetermined limit of propensity for settling. If so, indicate that the captured image reflects a fuel sample that is not acceptable. Otherwise, indicate that the captured image reflects a fuel sample that is acceptable.

6 Claims, 3 Drawing Sheets

(51) Int. Cl.
*G06T 7/00* (2017.01)
*G01N 21/59* (2006.01)
*G01N 21/25* (2006.01)
*G01N 1/44* (2006.01)
*G01N 21/01* (2006.01)
*G01N 21/17* (2006.01)

(52) U.S. Cl.
CPC .................. *G06T 7/90* (2017.01); *G01N 1/44* (2013.01); *G01N 21/255* (2013.01); *G01N 2021/0137* (2013.01); *G01N 2021/177* (2013.01); *G01N 2021/5915* (2013.01); *G01N 2021/5957* (2013.01); *G06T 2207/10024* (2013.01); *G06T 2207/20072* (2013.01)

(58) Field of Classification Search
CPC ......... G01N 21/255; G01N 2021/0137; G01N 2021/177; G01N 1/44; G06T 7/001; G06T 7/90; G06T 2207/20072; G06T 2207/10024
See application file for complete search history.

(56) References Cited

U.S. PATENT DOCUMENTS

| | | | |
|---|---|---|---|
| 6,598,464 B1* | 7/2003 | Rossi | G01N 15/0227 356/70 |
| 9,664,627 B2* | 5/2017 | Horstmeyer | F16N 29/00 |
| 2010/0238431 A1* | 9/2010 | Johnson | G01J 3/02 356/216 |

OTHER PUBLICATIONS

Written Opinion of The International Searching Authority published Nov. 8, 2018 (Year: 2018).*

Abellaneda et al; "Lubricating Oils Evaluation of Dispersancy Capacity of Lubricating Oils and the Impact of Biofuels on Lubricant Dispersancy"; ASTM International. JOU, ASTM International, US; vol. 8; No. 7; Jul. 1, 2011; pp. 126-141.

* cited by examiner

No. 1

No. 2

No. 3

No. 4

No. 5

FUEL COMPATIBILITY AND STABILITY ANALYZER

CROSS-REFERENCE TO RELATED APPLICATIONS

This application claims the benefit of provisional Application Ser. No. 62/429,624 filed Dec. 2, 2016, under 35 U.S.C. 119(e).

TECHNICAL FIELD

The present disclosure is directed to systems for measuring fuel compatibility and stability and, in particular, systems for autonomously measuring fuel compatibility and stability.

BACKGROUND

Heavy fuel oil (also referred to as marine fuels) is conventionally used in large format internal combustion engines, for example, engines used in marine vessels and power stations, and in refineries to heat distillation columns. Heavy fuel oil may also be consumed in distillation processes (for example, cracking and/or hydrocracking) to re-extract more noble products from the heavy fuel oil.

Heavy fuel oil is generally unstable, and are prone to settling of its constituents. The settling of the certain precipitants may cause deposits to form at the bottom of storage tanks holding the heavy fuel oil. In instances in which the liquid is removed and the precipitants remain, damage may be caused to an engine that consumes precipitants in an unacceptably high amount.

Conventional testing methodologies have been presented (for example, ASTM D4740) that govern determining the cleanliness of the heavy fuel oil. However, such test methodologies require significant human intervention and are prone to inaccuracies.

Accordingly, fuel sampling systems that exhibit improved reliability and consistent performance may be desired.

SUMMARY

In one embodiment, a fuel sampling system includes an optical capture device and an analysis computing device that stores logic for implementing an evaluation sequence. During the evaluation sequence, the analysis computing device performs at least the following: receive a captured image from the optical capture device, identify areas of highest contrast in the captured image, and determine if the areas of highest contrast define a ring. If the areas of highest contrast define a ring, evaluate a contrast ratio between the ring and areas outside of the ring, and determine if the captured image reflects a fuel sample that exceeds a predetermined limit of propensity for settling. If so, indicate that the captured image reflects a fuel sample that is not acceptable. Otherwise, indicate that the captured image reflects a fuel sample that is acceptable.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Reference will now be made in detail to embodiments of fuel sampling apparatuses. Various embodiments of fuel sampling apparatuses will be described in more detail herein.

As discussed hereinabove, heavy fuel oil that is allowed to have its constituents settle may result in damage to an engine that consumes the precipitants in an unacceptably high amount. Bulk heavy fuel oil, when store for extended periods of time, tends to precipitate its asphaltene content out of solution with the remaining liquid, thereby forming sludge in tanks. If ingested into the fuel system of an engine, the sludge has the potential to block filters and pipes, leaving tanks with an unpumpable residue.

Further, current emissions control regulations have imposed Emission Control Areas (ECAs) within which operators of vessels are prevented from consuming fuels having more than 0.10% sulfur. Because of the price difference between heavy fuel oils and marine gas oils that satisfy the requirements of the emission control area, vessel operators may prefer to use heavy fuel oils when outside of ECAs and switch to marine gas oils only when the vessel is present in the ECA.

When a vessel switches its fuel source, the switch needs to be conducted effectively so as to avoid any damage to the engine, to maintain engine operation and efficiency, and to ensure that the emissions limits are not exceeded. The International Convention for the Prevention of Pollution from Ships (MARPOL) requires vessels using separate fuel oils to develop and utilize written procedures showing how the fuel oil change-over is to be carried out, allowing sufficient time for the heavy fuel oil service system to be flushed of all heavy fuel oils exceeding the applicable sulfur content prior to the vessel's entry into an ECA.

Additionally, industry best practices are to avoid mixing fuels from different sources and with different formulations, as arbitrary commingling can lead to incompatibility problems and a loss of stability in the resultant blend. For example, when a heavy fuel oil with high asphaltene content is mixed with a low-gravity distillate with a predominance of paraffinic aliphatic hydrocarbons, the solvency reserve can be depleted and asphaltenes can flocculate and precipitate as sludge.

Although fuel incompatibility is not a common phenomenon, the likelihood of fuel incompatibility increases in conjunction with fuel switching, such as when a vessel switches fuel when entering and leaving an ECA. Compatibility problems must be treated as a critical concern as it can result in power failure, fuel systems can become clogged, and the job of correcting the failure is both difficult and time consuming.

The present disclosure is directed to fuel sampling systems that evaluate a fuel sample or evaluate a plurality of fuel samples to determine if the fuel is stable and/or to determine if a plurality of fuels are compatible with one another.

Figure 1:
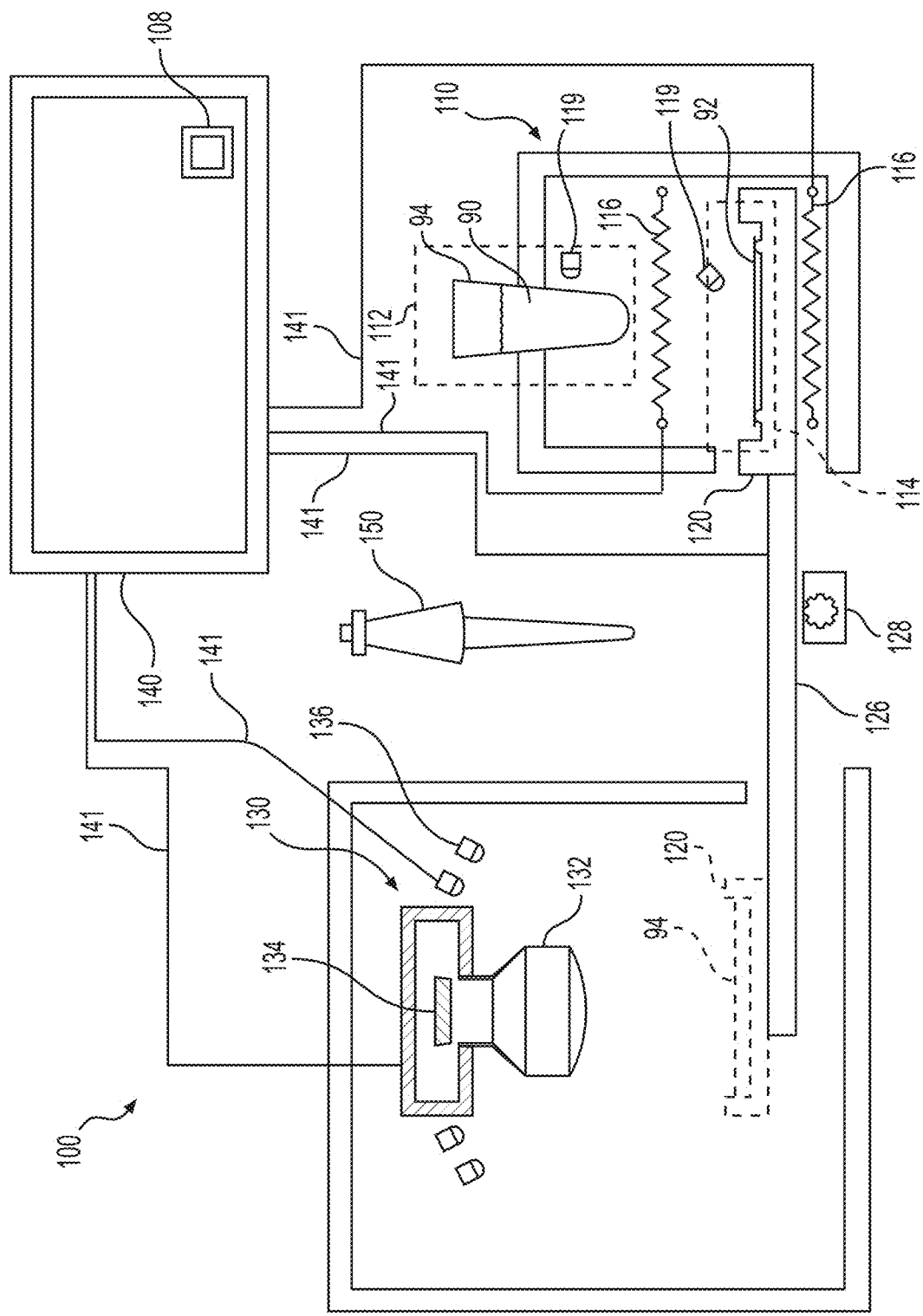
FIG. 1 depicts a schematic perspective view of a fuel sampling system according to one or more embodiments shown or described herein.

Referring now to FIG. 1, an embodiment of the fuel sampling system 100 is schematically depicted. In this embodiment, the fuel sampling system 100 includes an oven 110, an optical capture device 130, and an analysis computing device 140. The fuel sampling system 100 may also include a sample vial 94, a sample medium holder 120, and a sample dispenser 150. The components of the fuel sampling system 100 may be sufficiently miniaturized such that the components can fit within a hand-carryable case.

In operation, a user may dispense a fuel sample 90 that is to be tested into a sample vial 94. The fuel sample 90 may be heated to ensure that the fuel of the fuel sample 90 is flowable and is able to be well mixed. At least a portion of the volume of the fuel sample 90 may be introduced to a sample medium 92. The sample medium 92 that is now wetted by the fuel sample 90 may be introduced to the oven 110, such that the sample medium 92 is allowed to dry for a predetermined time or until a predetermined temperature of the sample medium 92 is reached, and the fuel sample is allowed to disperse through at least a portion of the sample medium 92.

Once the sample medium 92 is allowed to dry and the fuel sample 90 wicks in a generally outward direction through the sample medium 92, the sample medium 92 is removed from the oven 110 and positioned for optical analysis. The sample medium 92 is positioned proximate to the optical capture device 130. The optical capture device 130 gathers an electronic image and communicates the electronic image to the analysis computing device 140. The analysis computing device evaluates the electronic image of the sample medium 92 and provides an indication of acceptability of the fuel sample 90. The determination of the acceptability, along with the electronic image, may be stored in electronic storage for subsequent evaluation or validation of the determination of acceptability.

Still referring in detail to FIG. 1, the oven 110 is adapted to heat the fuel sample 90 to be tested, along with a sample medium 92 to which at least a portion of the fuel sample 90 is applied to perform the analysis. In one embodiment, the oven 110 may control regions of differing temperatures, such that a fuel sample region 112 of the oven 110 may heat a fuel sample 90 at a first temperature, and a sample medium region 114 of the oven 110 may heat a sample medium 92 to a second temperature different than the first temperature. The oven 110 may include at least one heater element 116 that generates heat and is controllable by the analysis computing device 140 to maintain the temperature of the oven 110 within a desired temperature range. In one embodiment, the oven 110 may hold the fuel sample 90 at about 93° C. and the sample medium 92 at about 100° C. In one embodiment, the heating element 116 may be a resistive heater, an induction coil, or the like. The oven 110 may also include a plurality of temperature sensors 119, for example thermocouples or infrared temperature sensors to measure the temperature of the oven 110 itself, or of the fuel sample 90 and the sample medium 92 while they are positioned proximate to the oven 110. In some embodiments, the fuel sampling system 100 may include a notification device 108 that indicates to a user that a condition has been reached (for example, that the fuel sample 90 has reached a pre-determined temperature) or that performance of an operation is required (for example, that the fuel sample 90 needs to be deposited on the sample medium 92; or that a soiled sample medium 92 needs to be discarded).

In some embodiments, the oven 110 may include an agitator 118, for example, a vibrator or an oscillator, that agitates the fuel sample 90 in the sample vial 94 to ensure good mixing of fuel sample 90 prior to the fuel sample 90 being introduced to the sample medium 92.

In the depicted embodiment, the fuel sampling system 100 also includes a sample dispenser 150. The sample dispenser 150 may be an automated or a manual pipette that allows for a predetermined volume of the fuel sample 90 to be removed from the sample vial 94 and to be dispensed onto the sample medium 92.

The fuel sample system 100 also includes a sample medium holder 120. The sample medium 92 may be filter paper such as Whatman paper No. 2 Qualitative Filter Paper available from Whatman, Inc., 9 Bridgewell Place, Clifton, N.J. 07014 USA. The sample medium 92 may be positioned on the sample medium holder 120. According to some test procedures, the sample medium holder 120 holding the sample medium 92 may be positioned in the sample medium region 114 of the oven 110 prior to the fuel sample 90 being dispensed onto the sample medium 92. In some embodiments, the sample medium holder 120 may be repositioned into and out of the oven 110 on a conveyor system 126. In some embodiments, the conveyor system 126 may include a motor 128 that drives the repositioning of the conveyor system 126 in general, and the sample medium holder 120 in particular. In some embodiments, the conveyor system 126 may be in electronic communication with the analysis computing device 140, and the operation of the conveyor system and the motor 128 may be controlled by the analysis computing device 140.

The fuel sample system 100 further includes an optical capture device 130. In the depicted embodiment, the optical capture device 130 includes a lens 132 and an image sensor 134. The image sensor 134 may be any of conventionally available image sensors, including semiconductor charge-coupled devices (CCDs) or complementary metal-oxide-semiconductor (CMOS) or N-type medal-oxide-semiconductor (NMOS). The optical capture device 130 may also include a lighting system 136. In some embodiments, the optical capture device 130 is positioned within an enclosure 104, such that environmental light does not affect the image captured by the optical capture device. Instead, the lighting system 136 provides all or nearly all of the light used during an image capture operation, such that the lighting conditions are consistent across multiple image capture operations.

The optical capture device 130 may be in electronic communication with the analysis computing device 140, and the settings and the operation of the optical capture device 130 may be controlled by the analysis computing device 140. After the optical capture device 130 captures the image of the sample medium 92, the image may be electronically communicated to the analysis computing device 140.

Figure 2:
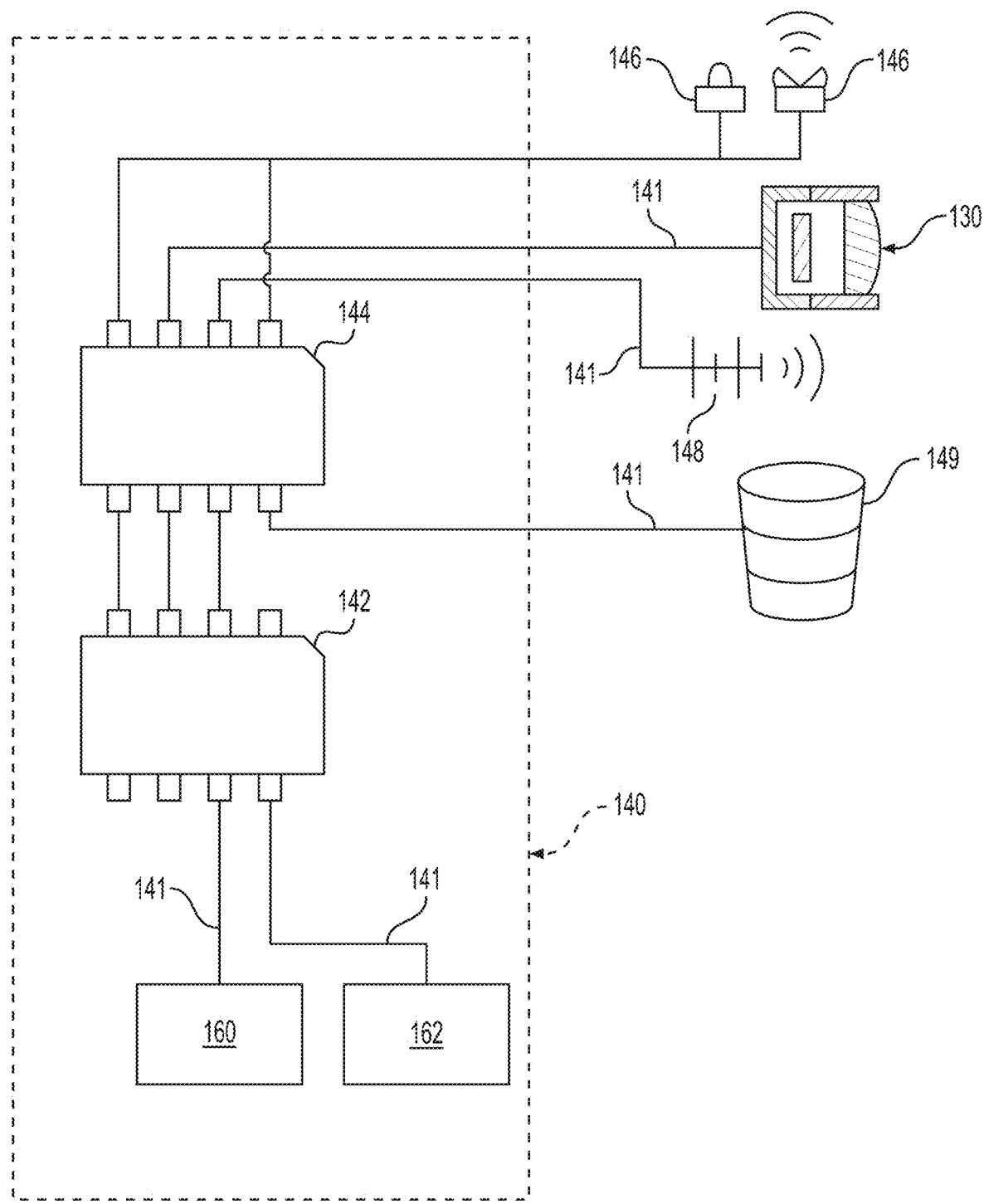
FIG. 2 depicts a schematic perspective view of an analysis computing device of a fuel sampling system according to one or more embodiments shown or described herein.

Referring now to FIG. 2, the analysis computing device 140 may include a memory component 142, a processor 144, input/output hardware 146, network interface hardware 148, and a data storage component 149 (which may store images gathered by the optical capture device 130 of the sample mediums and a database of the determination of the acceptability of the sample media). The memory component 142 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the fuel sampling system 100 and/or external to the fuel sampling system 100.

The memory component 142 may store operating logic 160 and evaluation logic 162. The operating logic 160 and the evaluation logic 162 may each include a plurality of different pieces of logic, each of which may be embodied as a computer program, firmware, and/or hardware, as an example. A communications path 141 is also depicted in FIG. 1 and may be implemented as a bus or other communication interface to facilitate communication among the components of the fuel sampling system 100.

The processor 144 may include any processing component operable to receive and execute instructions (such as from a data storage component 149 and/or the memory component 142).

The operating logic 160 may cause the processor 144 to instruct the various components of the fuel sampling system 100 to perform their designated functions, for example, for the oven to maintain certain pre-determined temperature, for the conveyor system to control movement of the sample medium holder, and for the image capture device 130 to capture an image of a sample medium. The operating logic 160 may adjust the instructions that the processor 144 delivers based on inputs received from various input hardware, for example, a timer or the temperature sensors of the oven.

The evaluation logic 162 may cause the processor 144 to execute an evaluation sequence in which a captured image that is received from the image capture device 130 and that corresponds to a respective sample medium is autonomously evaluated to determine if the fuel sample has a high or low propensity for settling.

Figure 3:
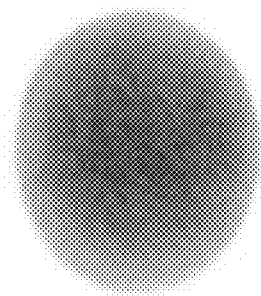
FIG. 3 depicts ASTM International reference standards that reflect known indications of acceptability for given fuel samples.
Figure 3:
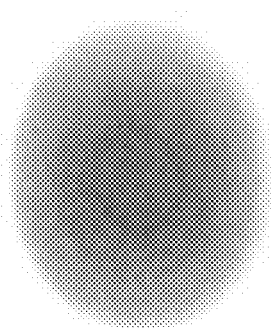
Figure 3:
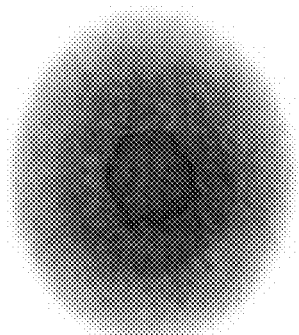
Figure 3:
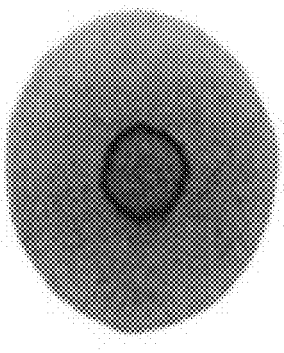
Figure 3:
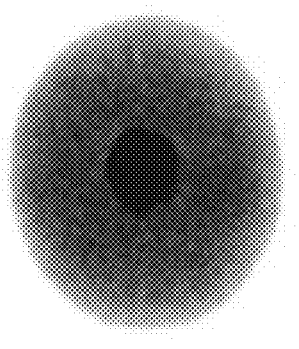

Referring now to FIG. 3, ASTM (formerly American Society for Testing and Materials) International reference standards are reproduced that reflect known indications of acceptability for given fuel samples. In operation, a liquid fuel sample is deposited in the approximate center of a sample medium. The liquid fuel sample disperses in a generally radial direction outward from the location of deposition of the liquid fuel sample. Depending on the quality of the liquid fuel sample, the resulting stain on the sample medium will vary. For example, for a liquid fuel sample that is stable and not prone to settling, the sample medium will reflect a homogenous or near homogenous oil stain (i.e., reference spot 1). For a liquid fuel sample that is unstable and prone to settling, the sample medium will reflect a well-defined inner ring (i.e., reference spot 3). Fuel samples with increasing instability and increasing tendency for settling will exhibit oil stains with increasingly well-defined inner rings, thicker rings, and darker or nearly dark central areas within the inner ring (i.e., reference spots 4 and 5).

Referring collectively to FIGS. 2 and 3, the evaluation logic 162 of the present disclosure includes instructions that cause the processor 144 to evaluate the captured image from the image capture device 130, determine if an inner ring is present in the sample medium, determine the severity of the inner ring, and make a determination of acceptability or unacceptability of a fuel sample based on the inner ring and/or the darkness of the central area within the inner ring.

In one embodiment, the evaluation logic 162 includes instructions that cause the processor to identify areas of the oil stain on the sample medium by evaluating the image according to chromatic criteria. The evaluation logic 162 may include instructions that cause the processor to determine the highest contrast area of the captured image. The evaluation logic 162 may instruct, for a given color channel (i.e., red-green-blue) of the captured image, to calculate a histogram of brightness values for all pixels in the area of analysis. The evaluation logic 162 may instruct to search the histogram for the highest variation. If the variation is less than a predetermined low limit, the evaluation logic 162 may instruct the processor to start the above-described operations with other color channels to determine which of the color channels generates a variation greater than a predetermined lower limit. The highest variation corresponding to the color value obtained is selected to be a threshold equal to the brightness value corresponding to the highest change.

The evaluation logic 162 may then instruct the processor to binarize the captured image with the determined threshold to obtain the shape and location of the most contrasting area. As is conventionally known, the binarization of the analyzed area is to assign the highest-contrast area. The evaluation logic 162 may instruct the processor to calculate the center of the highest contrasted area that is used as the center of the overall task.

The evaluation logic 162 may instruct the processor to search for a possible ring in the highest contrasting area as previously defined. By radial scanning of the center of brightness values to the periphery, inside the area of highest contrast, the processor may determine the limits of the possible ring, if any, as being those in which a localized variation in brightness is detected. If a ring is found, the evaluation logic 162 may instruct the processor to add a denotation to the binarized captured image.

The evaluation logic 160 may instruct the processor to analyze one or more areas interior to the identified ring, if any. The evaluation logic 160 may evaluate regions of the captured image at positions inside of the identified ring as compared to regions of the captured image at positions outside of the identified ring. Variations between respected regions may be evaluated according to the histogram with different chromatic criteria such as the brightness at positions inside of the highest contrast region as compared to positions outside of the highest contrast region.

The evaluation logic 160 may instruct the processor to combine the binary images of each phase in a single image file. During the previous phases described above, the captured image that is evaluated may be filtered by a digital filter so as to improve the representation of areas in the captured image. The evaluation logic 160 may instruct the processor to calculate a set of parameters of each identified area of the oil stain of the captured image. The evaluation logic 160 may instruct the processor to calculate an average opacity, a mean outside diameter and a surface associated with each area using the pixel values of the captured image, defined by the binarized image, and matched by geometric superposition.

The evaluation logic 160 may instruct the processor to output average brightness values of the captured image of the highest contrast region (which may correspond to an oil stain ring on the sample medium) and average brightness values outside of the highest contrast region. The evaluation logic 160 may also instruct the processor to calculate a contrast ratio between the locations corresponding to the high contrast region and locations outside of the high contrast region. The evaluation logic 160 may further instruct the processor to output whether the contrast ratio exceeds a pre-determined maximum, which indicates that the fuel sample exceeds the pre-determined limits for instability and propensity for settling.

The evaluation logic 160 may instruct the processor to store the captured image, the analysis, and/or the determination of acceptability to the data storage component 149, so that the data can be evaluated at a subsequent time. When such data is maintained in the data storage component 149, a need to maintain the stained sample media is eliminated.

In some liquid fuel evaluation operations, a single fuel source may be evaluated using the fuel sampling system of the present disclosure to determine if the fuel sample exceeds the pre-determined limits for instability and propensity for settling. In other liquid fuel evaluation operations in which a combination of fuels may lead to settling or instability, the plurality of fuels may be combined in an even ratio and then evaluated using the fuel sampling system of the present disclosure to determine if the combined fuel sample exceeds the pre-determined limits for instability and propensity for settling. In yet other liquid fuel evaluation operations in which a first fuel is being added to a second fuel in a known ratio, a fuel specimen may be blended according to that known ratio and then evaluated using the fuel sampling system of the present disclosure to determine if the combined fuel sample exceeds the pre-determined limits for instability and propensity for settling.

It should now be understood that fuel sampling systems according to the present disclosure provide for highly-repeatable and accurate evaluations of fuel samples. The evaluation logic eliminates the need for human evaluation of an oil stain on a sample medium, which previously has proven to be unreliable. Through autonomous control of the sample media preparation and evaluation, sample media preparation may be improved by minimizing any variation. Capture and storage of a digital image of the sample medium may allow for subsequent re-evaluation of a sample media, which would otherwise have been modified due to the continued spread of the fuel sample over time. Fuel sampling systems according to the present disclosure allow minimally trained users to perform a test of a fuel sample with highly accurate results.

It is noted that the terms "generally" and "substantially" may be used herein to represent the inherent degree of uncertainty that may be attributed to any quantitative comparison, value, measurement, or other representation. These terms are also used herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A fuel sampling system, comprising:
an optical capture device; and
an analysis computing device that stores logic for implementing an evaluation sequence in which the analysis computing device performs at least the following:
receive a captured image from the optical capture device;
identify areas of highest contrast in the captured image;
determine if the areas of highest contrast define a ring;
if the areas of highest contrast define a ring, evaluate a contrast ratio between the ring and areas outside of the ring; and
determine if the captured image reflects a fuel sample that exceeds a predetermined limit of propensity for settling based on whether the contrast ratio exceeds a predetermined maximum, and if so,
indicate that the captured image reflects a fuel sample that is not acceptable,
otherwise, indicate that the captured image reflects a fuel sample that is acceptable.

2. The fuel sampling system of claim 1, further comprising an oven, a sample holder, and a conveyor system, wherein the analysis computing device further stores logic for implementing an operation sequence in which the analysis computing device performs at least the following:
heats the oven to a pre-determined temperature;
maintains the sample holder within the oven for either a pre-determined time or until a pre-determined temperature has been reached; and
autonomously moves the sample holder from the oven to a position proximate to the optical capture device.

3. The fuel sampling system of claim 1, wherein the logic of the evaluation sequence further instructs the analysis computing device to store the captured image in a data storage component.

4. The fuel sampling system of claim 1, wherein the logic of the evaluation sequence further instructs the analysis computing device to store the determination of whether the fuel sample is acceptable in a data storage component.

5. The fuel sampling system of claim 2, wherein the oven comprises a fuel sample region and a sample medium region.

6. The fuel sampling system of claim 5, wherein the oven maintains the fuel sample region at a first temperature and the sample medium region at a second temperature that is different than the first.

* * * * *